United States Patent [19]

Diamond et al.

[11] Patent Number: 4,515,718

[45] Date of Patent: May 7, 1985

[54] AMIDINOUREAS

[75] Inventors: Julius Diamond, Morris Plains, N.J.; George H. Douglas, Malvern, Pa.

[73] Assignee: William H. Rorer, Inc., Fort Washington, Pa.

[21] Appl. No.: 429,917

[22] Filed: Sep. 30, 1982

Related U.S. Application Data

[60] Division of Ser. No. 118,826, Feb. 5, 1980, Pat. No. 4,353,842, which is a continuation of Ser. No. 942,247, Sep. 14, 1978, Pat. No. 4,204,000, which is a continuation-in-part of Ser. No. 787,673, Apr. 14, 1977, abandoned, which is a division of Ser. No. 558,187, Mar. 31, 1975, Pat. No. 4,060,635.

[51] Int. Cl.$^3$ ............... C07D 223/02; C07D 221/00
[52] U.S. Cl. .................. 260/239 B; 260/239 BC; 548/300; 548/356; 548/567; 546/231; 544/224; 544/335; 544/400
[58] Field of Search ............ 260/239 B, 239 BC; 548/567, 300, 356; 544/224, 335, 400; 546/231

[56] References Cited

U.S. PATENT DOCUMENTS 3,830,839  8/1974  Diana ................................. 546/231
3,903,084  9/1975  DuCharme et al. ................ 548/567

Primary Examiner—Donald G. Daus
Assistant Examiner—William A. Teoli, Jr.
Attorney, Agent, or Firm—James A. Nicholson; John C. Smith, Jr.

[57] ABSTRACT

A novel method of treating gastrointestinal, spasmolytic and ulcerogenic disorders by the administration of amidinoureas is disclosed.

3 Claims, No Drawings

AMIDINOUREAS

This is a division of application Ser. No. 118,826 filed Feb. 5, 1980 now U.S. Pat. No. 4,353,842 which is a continuation of application Ser. No. 942,247 filed Sept. 14, 1978 now U.S. Pat. No. 4,204,000 which is a continuation-in-part application of pending application Ser. No. 787,673 filed Apr. 14, 1977 now abandoned which is a divisional application of Ser. No. 558,187 filed Mar. 31, 1975 which is now U.S. Pat. No. 4,060,635.

The present invention relates to a new method for treating gastrointestinal, spasmolytic and ulcerogenic disorders by the administration of amidinoureas.

BACKGROUND OF THE INVENTION

The pharmaceutical compositions which have been used as gastric antisecretory and spasmolytic agents have been such as atropine, homatropine, propantheline bromide, dicyclomine hydrochloride and other compounds which are structurally dissimiliar to the biguanides of this invention. Due to the anticholinergic properties of these compounds, they are known to produce undesirable side effects such as mydriasis, xerostomia, cyclopegia and other unwanted effects.

There have been a number of 1-aryl biguanides described in the literature. They have been proposed for use as antidiabetics, anorexigenic or antimalarial agents. J. H. Burn and J. R. Vane, however, in the *Brit. J. Pharmacol.* (1948), 3:346-9 tested 1-(p-chlorophenyl)-biguanide for its ability to reduce gastric secretion. Their findings determined that little or no reduction of gastric secretion was associated with this compound. Contrary to this belief:

We have unexpectedly found that certain amidinoureas possess valuable pharmacologic properties and these compounds then unexpectedly possess useful gastric antisecretory and spasmolytic properties.

We have also found that these amidinoureas are substantially free of the anticholinergic side effects which accompany gastric antisecretory and spasmolytic agents.

We have further found that these amidinoureas have a low order of toxicity.

We have still further found a simple and effective method for treating gastrointestinal disorders and diseases, such as duodenal and peptic ulcers.

DESCRIPTION AND PREFERRED EMBODIMENTS

The present invention describes a method for treating gastrointestinal hyperacidity, gastrointestinal spasms or gastrointestinal ulcerations in human or mammal in need thereof by the oral or parenteral administration of an effective amount of an amidinourea of formula I or its tautomeric form II when R is hydrogen:

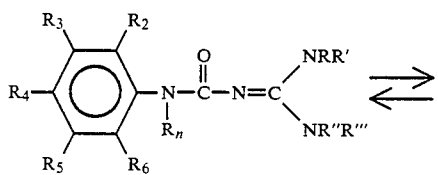

I

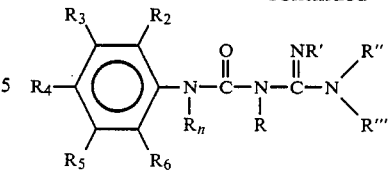

II where:
$R_2$, $R_3$, $R_4$, $R_5$ and $R_6$ may be the same or different and are:
hydrogen,
halo,
loweralkyl,
haloloweralkyl,
nitro,
loweralkoxy,
hydroxy,
arloweralkoxy,
acyloxy,
cyano,
haloloweralkoxy or
loweralkylsulfonyl;
R and R' are hydrogen or loweralkyl;
R" and R'" are
hydrogen,
loweralkyl,
loweralkenyl,
cycloalkenyl,
cycloalkylloweralkyl,
cycloalkyl,
aralkyl,
loweralkynyl,
haloalkyl,
hydroxyalkyl,
alkoxyalkyl,
cyanoalkyl,
aminoalkyl,
mono- and di- loweralkylaminoalkyl,
carbamoylalkyl,
mono- and di- carbamoylalkyl,
carboxyalkyl,
alkoxycarbonylalkyl,
aralkoxycarbonylalkyl,
formyl,
acyl,
acylalkyl,
alkylsulfonyl or
aralkylsulfonyl;
R" and R'" together may form a 5-7 atom ring which may include 0-2 hetero atoms of N, O or S;
$R_n$ is hydrogen or it may be loweralkyl provided at least one of R, R', R" and R'" is other than hydrogen; and the non-toxic acid addition salts thereof.

Compounds of this invention which are preferred include those where:
$R_2$, $R_3$, $R_4$, $R_5$ and $R_6$ are
hydrogen,
halo,
loweralkyl,
haloloweralkyl,
nitro,
hydroxy or
loweralkoxy; and R' and $R_n$ are hydrogen or loweralkyl and
R" and R'" are hydrogen or alkyl; provided R, R', R" and R'" are not all hydrogen at the same time.

The compounds of formula I or II of the present invention exist as tautomeric forms when a proton is present on the second nitrogen atom of the amidinourea chain. As with tautomers certain compounds would naturally exist in one form or the other depending on their character as discussed in *Journal of Organic Chemistry*, 33, 1968 p. 552.

The more preferred compounds of this invention include those where:
$R_2$ is hydrogen or loweralkyl;
$R_3$ and $R_5$ are hydrogen, hydroxy or loweralkoxy;
$R_4$ is
  hydrogen,
  loweralkyl,
  hydroxy,
  loweralkoxy or
  halo;
$R_6$ is
  hydrogen,
  loweralkyl,
  nitro,
  alkoxy or
  halo;
R and $R_n$ are hydrogen or loweralkyl; and
R' and R" are hydrogen or alkyl; provided R, R', R" and R'" are not all hydrogen at the same time.

The most preferred compounds of this invention are those where:
$R_2$ is
  hydrogen,
  methyl or
  ethyl;
$R_3$ is
  hydrogen,
  hydroxy or
  methoxy;
$R_4$ is
  hydrogen,
  methyl,
  ethyl,
  hydroxy,
  methoxy,
  chloro or
  bromo;
$R_5$ is
  hydrogen,
  hydroxy or
  methoxy;
$R_6$ is
  hydrogen,
  methyl,
  ethyl,
  nitro,
  methoxy,
  ethoxy,
  chloro,
  bromo or
  fluoro;
R and $R_n$ are
  hydrogen,
  methyl or
  ethyl; and
R' and R" are
  hydrogen,
  methyl,
  ethyl,
  propyl,
  i-propyl,
  butyl,
  i-butyl,
  sec-butyl,
  t-butyl,
  pentyl,
  hexyl or;
  heptyl;
provided R, R', R" and R'" are not all hydrogen at the same time.

A special embodiment of this invention comprises compounds which have:
$R_2$-loweralkyl substitution;
$R_2$, $R_6$-diloweralkyl substitution;
$R_2$, $R_6$-loweralkyl, alkoxy substitution;
$R_2$, $R_6$-loweralkyl, halo substitution;
$R_2$, $R_6$-alkyl, nitro substitution;
$R_2$, $R_4$, $R_6$-triloweralkyl substitution, or
$R_2$, $R_4$, $R_6$-loweralkyl, dihalo substitution.

A further special embodiment of this invention comprises compounds which have:
$R_3$, $R_4$-hydroxy or alkoxy substitution;
$R_3$, $R_4$, $R_5$-hydroxy or alkoxy substitution;
$R_2$, $R_5$-dihalo substitution or
$R_2$, $R_6$-dihalo substitution.

A further special embodiment of this invention comprises compounds which have:
R, R', R" and R'" as hydrogen or loweralkyl substitution provided all are not hydrogen at the same time; or
R and R' are hydrogen or loweralkyl and R" and R'" are an alkyl group from 3 to 7 carbon atoms.

The compounds of formula I form the subject matter of U.S. Pat. No. 4,060,635, Nov. 29, 1977 incorporated herein by reference.

The following is an example which shows the properties of the compounds of this invention. This is to be construed as an illustration of said compounds and not as limitations thereof.

EXAMPLE

1-Amidino-3-(2-chloro-6-methylphenyl)urea

A quantity of 20 g. of 1-(2-chloro-6-methylphenyl)-biguanide is added to 200 ml of 10% hydrochloric acid and the mixture is refluxed for 3 hours. The reaction mixture is then filtered hot and then chilled. The material which separates is then filtered off and recrystallized from isopropanol/water to obtain 1-amidino-3-(2-chloro-6-methylphenyl)urea hydrochloride.

The free base is prepared by dissolving the salt in 200 ml. of water and adding a 10% sodium hydroxide solution until alkaline. The reaction mixture is then extracted with chloroform which is dried and evaporated to dryness to obtain 1-amidino-3-(2-chloro-6-methylphenyl)urea.

When the biguanides of Table I below are used in the above example in place of 1-(2-chloro-6-methylphenyl)-biguanide, then the corresponding product of Table II is obtained.

Table I 1-(2,6-dimethylphenyl)-5,5-(N-methyl-3'-azapentamethylene)biguanide
1-(2,6-dimethylphenyl)-5,5-(N-methyl-3'-azaheptamethylene)biguanide Table II 1-[(N,N-(N-methyl-3'-azapentamethylene)amidino]-3-(2,6-dimethylphenyl)urea
1-[N,N-(N-methyl-3'-azaheptamethylene)amidino]-3-(2,6-dimethylphenyl)urea The compounds corresponding to formula I are useful in treating gastrointestinal disorders such as hyperacidity, spasms and peptic and gastric ulcers. For these purposes they can be administered orally, parenterally or rectally. Administration by the oral route is preferred. Orally, these compounds may be administered in tablets, hard or soft capsules, aqueous or oily suspensions, dispersible powders or granules, emulsions, syrups or elixers. The optimum dosage, of course, will depend on the particular compound being used and the type and severity of the condition being treated. In any specific case, the appropriate dosage selected will further depend on factors of the patient which may influence response to the drug; for example, general health, age, weight, etc. of the subject being treated.

Although the optimum quantities for administration of the compounds I in accordance with the present invention will depend on the compound employed and the particular type of disease condition treated, oral dose levels of preferred compounds when administered to a mammal in dosages of 0.05 to 50 milligrans per kilogram of body weight per day are particularly useful. The preferred range is 0.1 to 20 mg/kg. Comparative dosages may be used in parenteral or rectal administration.

Compositions intended for oral use may be prepared according to methods known in the art for the manufacture of pharmaceutical compositions. Such compositions may contain one or more agents selected from the group consisting of sweetening agents, flavoring agents, coloring agents, preserving agents, etc. in order to provide a pharmaceutically elegant and palatable preparation.

Further, the active amidinourea may be administered alone or in admixture with other agents having the same or different pharmacological properties.

The composition may contain such selected excipients such as inert diluents such as calcium carbonate, lactose, etc.; granulating and disintegrating agents such as maize starch, alginic acid, etc.; lubricating agents such as magnesium stearate, etc.; binding agents such as starch gelatin, etc.; suspending agents such as methylcellulose, vegetable oil, etc.; dispersing agents such as lecithin, etc.; thickening agents such as beeswax, hard paraffin, etc.; emulsifying agents such as naturally-occurring gums, etc.; non-irritating excipients such as cocoa butter, polyethylene glycols, etc.; and the like. Further, in formulating these compounds for every 100 parts by weight of the composition, there may be present between 5 and 95 parts by weight of the active ingredient. The dosage unit form will generally contain between 0.1 mg. and about 500 mg. of the active ingredients of this invention. The preferred unit dose is between 1 mg. and about 50 mg. The compositions may be taken 1–8 times daily depending on the dosage unit required.

The dosage regimen in carrying out the methods of this invention is that which insures maximum therapeutic response until improvement is obtained and thereafter the minimum effective level which gives relief. Thus, in general, the dosages are those that are therapeutically effective in the treatment of ulcerogenic disease conditions or symptoms, such as duodenal and peptic ulcer. In general, the daily dose can be between about 0.1 mg/kg and 70 mg/kg (preferably in the range of 1–25 mg/kg/day), bearing in mind, of course, that in selecting the appropriate dosage in any specific case, consideration must be given to the patient's weight, general health, age and other factors which may influence response to the drug.

Various tests in animals have been carried out to show the ability of the compounds of this invention to exhibit reactions that can be correlated with anti-ulcerogenic activity in humans. These tests involve such as the effect of the amidinoureas of the formula I on gastric secretion, gastrointestinal spasm and their mucogenic effect. It has been found that the compounds of this invention when tested in the above variety of situations, show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compound or the vehicle immediately subsequent to the ligation of the stomach at the pyloric sphincter. The animals are sacrificed with chloroform at 4 hours post-drug administration, the stomach is removed and its contents are assayed for volume, pH and total acids.

A second gastric secretion test is carried out on dogs. This is outlined in the Handbook of Physiology, Section 6: Alimentary Canal, Volume II: Secretion, American Physiology Society, Washington, D.C., 1967.

It has been found that the compounds of this invention when subjected to the above gastric secretion tests display a marked ability to decrease gastric volume and gastric acidity. These tests are known to correlate well with gastric acitivity in humans and is a standard test used to determine antisecretory properties.

To determine the anti-ulcer effectiveness the following test is employed: Male Wistar rats (130–150 grams) are fasted for 24 hours, then given reserpine at 5 mg/kg i.p. Twenty-four hours later, the stomachs are removed and examined for ulceration. Ulcers are graded on a 0–4 scale and the number of ulcers is recorded. Pretreatment with the 1,5-disubstituted biguanide compounds of this invention produces a decrease in ulcer grade and the number of ulcers compared to the control reserpine-treated rats.

Determination of antispasmodic properties can be carried out by the procedure as outlined by D. A. Brodie and S. K. Kundrats in their article entitled "Effect of Drugs on Gastric Emptying in Rats", *Fed. Proc.* 24:714 (1965).

The biguanides of this invention have also been found to be mucogenic agents, that is, they increase the biosynthesis of mucopolysaccharides of the gastric mucous membrane which is a mechanism for inhibiting gastrointestinal ulcer. This property is determined by the test outlined in the *J. Pharm. Pharmac.*, 1970, 22, 143–4.

Mydriasis is detected by the procedure R. A. Turner, *Screening Methods in Pharmacology*, Academic Press, New York, and London, pp. 174–5, 1965. Acute toxicity is calculated according to the standard Litchfield-Wilcoxon procedure.

In view of the results of these tests the pharmacological data clearly indicates that the amidinoureas of the formula I substituted biguanides of this invention can be considered to be effective anti-ulcerogenic agents having active gastric antisecretory and antispasmodic properties which are substantially free of anticholinergic side effects and having a low toxicity.

We claim:

1. An amidinourea compound of the formula I or its tautomeric form II when R is hydrogen:

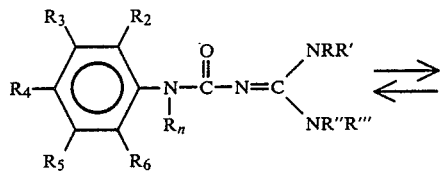

I

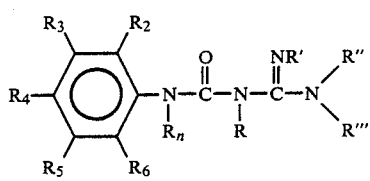

II where:

$R_2$, $R_3$, $R_4$, $R_5$ and $R_6$ may be the same or different and are
hydrogen,
halo,
loweralkyl,
haloloweralkyl,
nitro,
loweralkoxy,
hydroxy,
cyano,
haloloweralkoxy, or
loweralkylsulfonyl,
provided at least three of $R_2$, $R_3$, $R_4$, $R_5$ and $R_6$ are hydrogen;

R and R' are hydrogen or loweralkyl;

R" and R'" together with nitrogen form a 5–7 atom ring consisting of 3–6 carbon atoms and 1–2 nitrogen atoms;

$R_n$ is hydrogen or loweralkyl provided at least one of R, R', R" and R'" is other than hydrogen; and the non-toxic acid addition salts thereof.

2. An amidinourea compound according to claim 1 which is 1-[N,N-(N-methyl-3'-azapentamethylene)amidino]-3-(2,6-dimethylphenyl)urea.

3. An amidinourea compound according to claim 1 which is 1-[N,N-(N-methyl-3'-azaheptamethylene)amidino]-3-(2,6-dimethylphenyl)urea.

* * * * *